(12) United States Patent
Wang et al.

(10) Patent No.: US 11,958,012 B2
(45) Date of Patent: Apr. 16, 2024

(54) METHOD AND SYSTEM FOR REMOVING CARBON DIOXIDE FROM REACTION GAS, AND USE THEREOF

(71) Applicants: CHINA PETROLEUM & CHEMICAL CORPORATION, Beijing (CN); SINOPEC NANJING RESEARCH INSTITUTE OF CHEMICAL INDUSTRY CO., LTD., Jiangsu (CN)

(72) Inventors: Xiangyun Wang, Jiangsu (CN); Haitao Li, Jiangsu (CN); Ye Zhang, Jiangsu (CN); Li Xu, Jiangsu (CN); Yunsheng Zhao, Jiangsu (CN); Xiaolian Wu, Jiangsu (CN); Pinhua Yu, Jiangsu (CN)

(73) Assignees: CHINA PETROLEUM & CHEMICAL CORPORATION, Beijing (CN); SINOPEC NANJING RESEARCH INSTITUTE OF CHEMICAL INDUSTRY CO., LTD., Nanjing (CN)

( * ) Notice: Subject to any disclaimer, the term of this patent is extended or adjusted under 35 U.S.C. 154(b) by 189 days.

(21) Appl. No.: 17/482,415

(22) Filed: Sep. 22, 2021

(65) Prior Publication Data
US 2022/0032230 A1    Feb. 3, 2022

Related U.S. Application Data

(63) Continuation-in-part of application No. PCT/CN2019/127532, filed on Dec. 23, 2019.

(30) Foreign Application Priority Data

Mar. 22, 2019 (CN) .................. 201910222351.X (51) Int. Cl.
*B01D 53/62* (2006.01)
*B01D 53/14* (2006.01)
(Continued)

(52) U.S. Cl.
CPC ......... *B01D 53/62* (2013.01); *B01D 53/1425* (2013.01); *B01D 53/78* (2013.01);
(Continued)

(58) Field of Classification Search
CPC .... B01D 53/62; B01D 53/1425; B01D 53/78; B01D 53/96
(Continued)

(56) References Cited

FOREIGN PATENT DOCUMENTS

| CN | 101210186 A | 7/2008 |
|---|---|---|
| CN | 102675248 B | 3/2015 |

(Continued)

OTHER PUBLICATIONS

CN-108129254-A English translation (Year: 2018).*
International search report of PCT Patent Application No. PCT/CN2019/127532 dated Mar. 26, 2020.

*Primary Examiner* — Anita Nassiri-Motlagh (57) ABSTRACT

The present invention discloses a method for removing carbon dioxide from a reaction gas. The present invention fully utilizes the available heat in each part of the carbon dioxide removal system to reduce external heat exchange, and thereby significantly reduces the carbon dioxide content in the gas returned to the reactor, and also greatly reduces the steam consumption during the regeneration of the rich decarburizing solution. The present invention also discloses a system for removing carbon dioxide from the reaction gas and use thereof.

11 Claims, 2 Drawing Sheets

(51) Int. Cl.
  *B01D 53/78* (2006.01)
  *B01D 53/96* (2006.01)
(52) U.S. Cl.
  CPC ........ *B01D 53/96* (2013.01); *B01D 2251/606* (2013.01); *B01D 2257/504* (2013.01)
(58) Field of Classification Search
  USPC .................................................. 423/243.08
  See application file for complete search history.

(56) References Cited

FOREIGN PATENT DOCUMENTS

| | | | |
|---|---|---|---|
| CN | 108129254 A | 6/2018 | |
| JP | 5639814 B2 | 12/2014 | |

* cited by examiner

METHOD AND SYSTEM FOR REMOVING CARBON DIOXIDE FROM REACTION GAS, AND USE THEREOF

CROSS-REFERENCE TO RELATED APPLICATIONS

The present application is a Continuation-In-Part Application of PCT application No. PCT/CN2019/127532 filed on Dec. 23, 2019, which claims the benefit of Chinese Patent Application No. CN201910222351.X filed on Mar. 22, 2019. The contents of the above-identified applications are hereby incorporated by reference.

FIELD OF THE INVENTION

The present invention relates to a method for removing carbon dioxide in a reaction gas, a system for removing carbon dioxide in a reaction gas, and use thereof, and in particular, the present invention relates to a method for removing carbon dioxide from an ethylene oxide reaction circulation gas, a system for removing carbon dioxide from an ethylene oxide reaction circulation gas, and use thereof.

BACKGROUND OF THE INVENTION

High-purity ethylene is oxidized with pure oxygen to generate ethylene oxide (EO). During oxidation of ethylene to generate ethylene oxide, a certain amount of $CO_2$ is generated, and $CO_2$ must be removed from a synthesis circulation gas to maintain efficiency of a catalytic reaction.

With the development and use of new oxidation catalysts with high selectivity, the amount of ethylene used in the production of ethylene oxide is continuously reduced. At the same time, a concentration of $CO_2$ in the circulation gas is required to be lower, from the original 5 mol % to 2 mol %, and then to less than 1 mol %. To make modification under the original solvent and process conditions for decarbonizing of the circulation gas, a main method is to increase a split ratio of the circulation gas into a decarbonizing unit, i.e., from 25% to 50%, and then to 100% of the circulation gas. That is, by increasing an amount of the circulation gas that enters a decarbonizing absorption tower (reducing an amount of the gas that does not enter the decarbonizing absorption tower), the concentration of the residual $CO_2$ is reduced. However, when the circulation gas having a low temperature and a low water content that enters the high-temperature decarbonizing absorption tower for mass transfer with an aqueous decarburizing solution is greatly increased, the gas exiting from the tower takes away a large amount of heat and water steam, which makes a temperature of a rich liquid exiting from a bottom of the absorption tower decrease, so that an amount of water steam required for boiling a desorption solution in a regeneration tower is increased necessarily. That is, the energy consumption increases.

Since a partial pressure of $CO_2$ is always low during the decarbonizing process of the ethylene oxide synthesis circulation gas, i.e., the decarbonizing being in a lean liquid circulation operation state, it is more difficult to desorb $CO_2$ in the solution. To reduce an amount of residual $CO_2$ in a purified gas at an outlet of the absorption tower, it is necessary to make desorption and regeneration of a lean liquid more thorough and it is required to consume more steam.

Chinese patent CN 201210134232.7 mainly focuses on the regeneration part and develops new process procedures to improve the desorption quality of a decarburizing solution, so as to improve the decarbonizing efficiency and reduce energy consumption at the same time.

When all of the circulation gas passes through the decarbonizing unit, the amount of the circulation gas is increased manyfold, and the circulation gas in the absorption tower has a temperature of more than 100° C. However, it is required that the circulation gas returning to an oxidation reactor have a temperature of less than 40° C. To decrease the temperature of the circulation gas, a great amount of heat is taken away, and it is necessary that the steam consumption in the decarbonizing system increases. In order to minimize the increase in steam consumption, a new process must be further developed.

SUMMARY OF THE INVENTION

Directed against the technical problem in existing technologies, the present invention aims to provide a method for removing carbon dioxide from a reaction gas, a system for removing carbon dioxide from a reaction gas, and use thereof. The method and system in the present invention can adequately and effectively utilize heat inside the system, and can greatly save energy while ensuring that a content of residual carbon dioxide in a purified gas meets the criterion under the condition of greatly increasing the gas treatment capacity.

According to one aspect of the present invention, a method for removing carbon dioxide from a reaction gas is provided. The method comprises the following steps:

S1. Performing a heating treatment on the reaction gas from which carbon dioxide is to be removed by heat exchanging the reaction gas with a washing water to obtain a gas stream III;

S2. performing a decarbonizing treatment on the gas stream III obtained in step S1 by using a decarburizing solution to obtain a gas stream IV; and S3. cooling the gas stream IV to obtain a $CO_2$-removed purified gas, Wherein the washing water is first cooled by a cooling device, then exchanges heat with the gas stream IV, subsequently exchanges heat with the decarburizing solution, finally exchanges heat with the reaction gas from which carbon dioxide is to be removed, and after that returns to the cooling device for cooling circulation.

According to some embodiments of the present invention, in the step S1, the heating treatment is performed on the reaction gas from which carbon dioxide is to be removed by heat exchanging the reaction gas with the washing water and a regeneration gas.

According to a preferred embodiment of the present invention, it would be better if a temperature of the reaction gas is increased as much as possible. In this way, redundant heat in the regeneration gas and the washing water can be fully recycled, and the temperature of the gas entering an absorption tower can also be increased. Further, a temperature of a rich liquid discharged from the absorption tower can be increased, and steam needed for heating and desorption when the rich liquid is regenerated is reduced, which saves energy and reduces energy consumption.

In some specific embodiments, the temperature of the reaction gas is increased to 70° C. to 100° C., so as to fully recycle redundant heat from the regeneration gas and the washing water.

According to a preferred embodiment of the present invention, the step S1 comprises the following steps:

1A. dividing the reaction gas from which carbon dioxide is to be removed into a gas stream I and a gas stream II;

1B. heating the gas stream I by heat exchanging with a regeneration gas exiting from the top of a regeneration tower to obtain a gas stream Ia;

1C. heating the gas stream II by heat exchanging with the washing water to obtain a gas stream IIa; and 1D. mixing the gas stream Ia with the gas stream IIa to obtain the gas stream III.

According to a preferred embodiment of the present invention, a molar ratio of the gas stream I to the gas stream II is (0-70):(100-30), preferably (30-70):(70-30), and more preferably (40-60):(60-40).

According to the method of the present invention, the gas stream I exchanges heat with the regeneration gas exiting from the top of the regeneration tower and absorbs heat from the regeneration gas, so that the temperature of the gas stream I is increased; and the gas stream II exchanges heat with the washing water and absorbs the heat in the washing water, so that the temperature of the gas stream II is increased. According to the method of the present invention, on one hand, heat from the regeneration gas and from the washing water is used, so that the heat is recycled; and on the other hand, the temperature of the gas entering the absorption tower is increased. Further, the temperature of the rich liquid discharged from the absorption tower can be increased, and steam needed for heating and desorption when the rich liquid is regenerated is reduced, which saves energy and reduces energy consumption.

According to some embodiments of the present invention, in the step S2, carbon dioxide is removed from the gas stream III by using a decarburizing solution, to reduce a concentration of carbon dioxide in the gas stream III to a concentration that meet the requirement of a catalyst.

In some specific embodiments, the concentration of carbon dioxide in the gas stream III is reduced to be 0.1-1.0%.

According to a preferred embodiment of the present invention, preferably, the decarburizing solution is a lean liquid from the bottom of the regeneration tower, preferably a carbonate solution, and more preferably an activated hot potassium carbonate solution.

According to a preferred embodiment of the present invention, the step S2 comprises the following steps:

2A. allowing the gas stream III to countercurrent contact with a first stream of decarburizing solution to obtain a gas stream IIIa and a first stream of a first rich liquid; and 2B. allowing the gas stream IIIa to countercurrent contact with a second stream of the decarburizing solution to obtain the gas stream IV and a second stream of a rich liquid.

According to the method of the present invention, the washing water is first cooled to a temperature below 40° C., preferably below 33° C., by the cooling device. Then, the washing water exchanges heat with the gas stream IV to cool the gas stream IV, and the temperature of the washing water itself is increased. Then, the washing water exchanges heat with the second stream of the decarburizing solution to cool the second stream of the decarburizing solution, and the temperature of the washing water itself is further increased. Finally, the washing water exchanges heat with the gas stream II to transfers heat absorbed from the gas stream IV and the second stream of the decarburizing solution to the gas stream II, so as to increase the temperature and humidity of the gas stream II. After that, the washing water returns to the cooling device to continue the cooling circulation. In this process, heat in the system is circulated and recycled by using the washing water as a medium, which reduces heat loss and saves energy.

According to a preferred embodiment of the present invention, the washing water may first exchange heat with the gas stream II, then exchanges heat with the gas stream IV after being cooled to a temperature below 40° C. by the cooling device, and subsequently exchanges heat with the second stream of the decarburizing solution for circulation.

According to a preferred embodiment of the present invention, the first stream of the decarburizing solution and the second stream of the decarburizing solution are the lean liquid from the bottom of the regeneration tower respectively; and the first stream of the decarburizing solution directly countercurrent contacts with the gas stream III to obtain the first stream of the rich liquid; the second stream of the decarburizing solution first exchanges heat with a stream of the rich liquid having a lower temperature, then exchanges heat with the washing water, and finally countercurrent contacts with the gas stream IIIa to obtain the second rich liquid.

According to a preferred embodiment of the present invention, the second stream of the decarburizing solution first exchanges heat with the stream of the rich liquid having a lower temperature to be cooled, then exchanges heat with the washing water to be cooled to 60° C. to 95° C., preferably 65° C. to 90° C., and finally countercurrent contacts with the gas stream IIIa to obtain the second stream of the rich liquid.

According to a preferred embodiment of the present invention, the first stream of the rich liquid and the second stream of the rich liquid are mixed and return to the regeneration tower for regeneration. By heat exchanging between the first stream of the rich liquid having a lower temperature and the second stream of the decarburizing solution, on one hand, heat of the second stream of the decarburizing solution can be recycled and utilized, so that heat is recycled; and on the other hand, the temperature of the rich liquid is increased, so that steam needed for heating and desorption when the rich liquid is regenerated is reduced, which saves energy and reduces energy consumption.

According to a preferred embodiment of the present invention, the method further comprises:

By using heat contained in a regeneration gas exiting from the top of a regeneration tower, providing heat to a lithium bromide chiller of a cooling device to generate chilled-water, decreasing the temperature of the washing water, and then cooling the gas stream IV.

With respect to the circumstance where the catalyst requires that a content of water in a circulation gas should be lower than 0.3% and chilled water must be provided to reduce a content of saturated water in the purified gas returning to a reactor, the heat of the regeneration gas may be provided to a heat pump to generate steam which is provided to a lithium bromide chiller to generation chilled water with a temperature below 33° C. for cooling a decarbonized gas. In this way, the requirement of the catalyst can be met, and a great amount of steam needed by the lithium bromide chiller can also be saved without increasing energy consumption for decarbonizing.

According to some embodiments of the present invention, the method further comprises the following steps:

S0. dividing the reaction gas from a compressor into a gas stream A' and a gas stream B', the gas stream A' being treated according to the steps S1 to S3; and S4. mixing the gas stream B' and a purified gas obtained according to the steps S1 to S3 and recirculating back to the reactor.

According to a preferred embodiment of the present invention, a molar ratio of the gas stream A' to the gas stream B' is (70-100):(30-0), preferably (75-90):(25-10).

It is founded by the inventor during research that, by defining the ratio of the gas stream A' to the gas stream B' in the above range, a content of carbon dioxide in a gas circulating back to the reactor can be reduced significantly, or an amount of steam consumed when the rich liquid is regenerated is reduced.

According to another aspect of the present invention, a system for removing carbon dioxide from a reaction gas is provided. The system comprises:

a heating zone for performing heating treatment on the reaction gas from which carbon dioxide is to be removed; and a decarbonizing zone for receiving a gas from the heating zone and performing a decarbonizing and cooling treatment on the gas.

According to some embodiments of the present invention, the heating zone comprises at least one water washing tower for heat exchanging the reaction gas from which carbon dioxide is to be removed with a washing water.

According to some embodiments of the present invention, the water washing tower being provided with a reaction gas inlet, a reaction gas outlet, a washing water inlet, and a washing water outlet. The reaction gas inlet being used for receiving the reaction gas from which carbon dioxide is to be removed, the reaction gas outlet being connected to a reaction gas inlet of an absorption tower in the decarbonizing zone, the washing water inlet being connected to a washing water outlet of a lean liquid water cooler, the washing water outlet being connected to an inlet of a washing water cooling device.

According to a preferred embodiment of the present invention, the reaction gas inlet of the water washing tower being provided at a lower portion of a sidewall of the water washing tower, the reaction gas outlet of the water washing tower being provided at the top of the water washing tower, the washing water inlet of the water washing tower being provided at an upper portion of the sidewall of the water washing tower, the washing water outlet of the water washing tower being provided at a lower portion of the sidewall of the water washing tower.

According to the system of the present invention, the reaction gas enters the water washing tower from the bottom to the top, and the washing water enters the water washing tower from the top to the bottom to countercurrent contact with the reaction gas, so that the reaction gas adequately absorbs heat of the washing water to be heated and humidified. In this way, heat of the washing water can be utilized, and the temperature of the gas entering the absorption tower can also be increased. Further, the temperature of the rich liquid exiting from the absorption tower can be increased, and steam needed for heating and desorption when the rich liquid is regenerated is reduced, which reduces energy consumption.

According to a preferred embodiment of the present invention, a liquid waste outlet being provided at the bottom the water washing tower and used for discharging liquid waste accumulated in the water washing tower.

According to a preferred embodiment of the present invention, the system is further provided with a washing water supplement inlet connected to the washing water inlet of the water washing tower. The washing water supplement inlet being used for directly supplementing desalted water into the water washing tower, and then the desalted water enters a washing water cooler for circulation.

According to a preferred embodiment of the present invention, the heating zone further comprises at least one gas heat exchanger for heat exchanging the reaction gas from which carbon dioxide is to be removed with a regeneration gas exiting from the top of a regeneration tower.

According to a preferred embodiment of the present invention, the gas heat exchanger being provided with a reaction gas inlet, a reaction gas outlet, a regeneration gas inlet, and regeneration gas outlet. The reaction gas inlet being used for receiving the reaction gas from which carbon dioxide is to be removed, the reaction gas outlet being connected to the reaction gas inlet of the absorption tower in the decarbonizing zone, the regeneration gas inlet being connected to a gas outlet at the top of the regeneration tower, the regeneration gas outlet being connected to an inlet of a regeneration gas cooling device.

The gas heat exchanger is provided with a reaction gas channel and a regeneration gas channel. The reaction gas channel being connected to the reaction gas inlet and the reaction gas outlet respectively, and being used for circulating the reaction gas entering the gas heat exchanger. The regeneration gas channel being connected to the regeneration gas inlet and the regeneration gas outlet respectively, and being used for circulating the regeneration gas entering the gas heat exchanger.

According to the system of the present invention, the reaction gas exchanges heat with the regeneration gas in the gas exchanger. The temperature of the reaction gas is increased by the heat of the regeneration gas, and the temperature of the gas entering the absorption tower can be increased. Further, the temperature of the rich liquid discharged from the absorption tower can be increased, and steam needed for heating and desorption when the rich liquid is regenerated is reduced, which reduces energy consumption.

According to a preferred embodiment of the present invention, the reaction gas and the regeneration gas flow in countercurrent directions in the gas heat exchanger.

According to some embodiments of the present invention, the decarbonizing zone comprises at least one absorption tower for performing decarbonizing and cooling treatment on the gas from the heating zone.

According to a preferred embodiment of the present invention, the absorption tower being provided with a reaction gas inlet and a reaction gas outlet. The reaction gas inlet being connected to a gas outlet of the water washing tower and/or a gas outlet of the gas heat exchanger, and the reaction gas outlet is connected to a gas inlet of the reactor. In the absorption tower, the reaction gas enters from the bottom to the top, and countercurrent contacts with the decarburizing solution and the washing water to adequately perform decarbonizing and cooling treatment.

According to a preferred embodiment of the present invention, the absorption tower comprises a first absorption section, a second absorption section, and a cooling section disposed from the bottom to the top. The first absorption section, the second absorption section, and the cooling section are liquid-separated from one another, and only gas is allowed to pass through.

According to a preferred embodiment of the present invention, the first absorption section, the second decarbonizing absorption section, and the cooling section are separated from one another by a liquid collection tray, and liquid cannot pass through. The liquid collection tray being provided with a tray riser which allows gas pass through.

According to a preferred embodiment of the present invention, the first absorption section, the second absorption section, and the cooling section are respectively provided with at least one layer of filler or tower plate.

According to some embodiments of the present invention, the first absorption section being provided with a reaction gas inlet, a reaction gas outlet, a decarburizing solution inlet, and a decarburizing solution outlet. The reaction gas inlet being connected to the reaction gas inlet of the absorption tower, the reaction gas outlet being connected to a reaction gas inlet of the second absorption section, preferably a tray riser of a liquid collection tray, the decarburizing solution inlet being connected to a lean liquid outlet at the bottom of the regeneration tower, the decarburizing solution outlet being connected to a rich liquid inlet of a lean-rich liquid heat exchanger or to a rich liquid inlet of the regeneration tower.

According to a preferred embodiment of the present invention, the reaction gas inlet of the first absorption section being provided at a lower portion of a sidewall thereof, the reaction gas outlet of the first absorption section being provided at the top thereof, preferably connected to a tray riser of a liquid collection tray, the decarburizing solution inlet of the first absorption section being provided at an upper portion of the sidewall thereof, the decarburizing solution outlet of the first absorption section being provided at the bottom thereof.

According to the system of the present invention, in the first absorption section, the reaction gas enters from the bottom to the top, and countercurrent contacts with a first decarburizing solution entering from the upper portion to adequately perform decarburizing. The decarburizing solution absorbs the carbon dioxide in the reaction gas and at the same time transfers heat to the gas, a temperature of the decarburizing solution being decreased, so that a first stream of a rich liquid is obtained.

According to some embodiments of the present invention, the second absorption section being provided with a reaction gas inlet, a reaction gas outlet, a decarburizing solution inlet, and a decarburizing solution outlet. The reaction gas inlet being connected to the reaction gas outlet of the first absorption section, the reaction gas outlet being connected to a reaction gas inlet of the cooling section, preferably a tray riser of a liquid collection tray, the decarburizing solution inlet being connected to a decarburizing solution outlet of a lean liquid water cooler, the decarburizing solution outlet being connected to a rich liquid inlet of the lean-rich liquid heat exchanger or to a rich liquid inlet of a regeneration tower.

According to a preferred embodiment of the present invention, the reaction gas inlet of the second absorption section being provided at the bottom thereof, the reaction gas outlet of the second absorption section being provided at the top thereof, the decarburizing solution inlet of the second absorption section being provided at an upper portion of a sidewall thereof, the decarburizing solution outlet of the second absorption section being provided at a lower portion of the sidewall thereof.

According to the system of the present invention, in the second absorption section, the reaction gas enters from the bottom to the top, and countercurrent contacts with a second stream of the decarburizing solution entering from the upper portion to adequately perform decarbonizing. The decarburizing solution absorbs the carbon dioxide in the reaction gas, and at the same time a temperature of the decarburizing solution is increased, so that a second stream of a rich liquid is obtained.

According to some embodiments of the present invention, the cooling section being provided with a reaction gas inlet, a reaction gas outlet, a washing water inlet, and a washing water outlet. The reaction gas inlet being connected to the reaction gas outlet of the second absorption section, the reaction gas outlet being connected to the reaction gas outlet of the absorption tower, the washing water inlet being connected to a washing water outlet of a washing water cooling device, the washing water outlet being connected to a washing water inlet of a lean liquid water cooler.

According to a preferred embodiment of the present invention, the reaction gas inlet of the cooling section being provided at the bottom thereof, the reaction gas outlet of the cooling section being provided at the top thereof, the washing water inlet of the cooling section being provided at an upper portion of a sidewall thereof, the washing water outlet of the cooling section being provided at a lower portion of the sidewall thereof.

According to some embodiments of the present invention, the system further comprises a washing water cooling device for cooling the washing water. The washing water cooling device comprises at least one washing-water circulation-water cooler and at least one washing-water chilled-water cooler. The washing-water circulation-water cooler being provided with an inlet and an outlet, the inlet being connected to a washing water outlet of a water washing tower, the outlet being connected to an inlet of the washing-water chilled-water cooler. The washing-water chilled-water cooler being provided with an inlet and an outlet, the inlet being connected to the outlet of the washing-water circulation-water cooler, the washing water outlet being connected to the washing water inlet of a cooling section of the absorption tower.

According to a preferred embodiment of the present invention, the washing water cooler is further provided with a washing water supplement inlet and a washing water discharge outlet, the washing water supplement inlet being used for supplementing desalted water to the system, the washing water discharge outlet being used for discharging washing water that is polluted in the system.

Preferably, the washing-water circulation-water cooler and/or the washing-water chilled-water cooler are/is provided with a washing water supplement inlet and a washing water discharge outlet, the washing water supplement inlet being used for supplementing desalted water to the system, the washing water discharge outlet being used for discharging washing water that is polluted in the system.

Water quality of circulation washing water is monitored by a conductometer in real time to determine whether the washing water is polluted, and then discharging, supplementing, and replacing may be performed.

According to a preferred embodiment of the present invention, the washing-water chilled-water cooler is composed of a lithium bromide chiller and a heat pump, the heat pump being connected to a regeneration-gas gas heat exchanger in parallel. A regeneration gas from the regeneration tower enters the heat pump and provides heat to the heat pump so as to generate steam which being provided to the lithium bromide chiller for refrigeration, cold generated reduces a temperature of a circulation washing water to below 33° C.

With respect to the circumstance where the catalyst requires that a content of water in a circulation gas should be lower than 0.3% and chilled water must be provided to reduce a content of saturated water in the purified gas returning to a reactor, the above device may be used. In this way, the requirement of the catalyst can be met, and a great amount of steam needed by the lithium bromide chiller can also be saved without increasing energy consumption in decarbonizing.

According to some embodiments of the present invention, the system further comprises a decarburizing solution heat exchanging device used for conducting heat exchange on a decarburizing solution. The decarburizing solution exchanges heat with the rich liquid and washing water respectively in the decarburizing solution heat exchanging device.

According to a preferred embodiment of the present invention, the decarburizing solution heat exchanging device comprises at least one lean-rich liquid heat exchanger and at least one lean liquid water cooler. The lean-rich liquid heat exchanger being used for heat exchanging a second stream of the decarburizing solution with a stream of the rich liquid with a lower temperature selected from a first stream of a rich liquid and a second stream of a rich liquid, and the lean liquid water cooler being used for heat exchanging the second stream of the decarburizing solution with the washing water for cooling.

According to a preferred embodiment of the present invention, the lean-rich liquid heat exchanger being provided with a decarburizing solution inlet, a decarburizing solution outlet, a rich liquid inlet, and a rich liquid outlet. The decarburizing solution inlet being connected to a lean liquid outlet at the bottom of a regeneration tower, the decarburizing solution outlet being connected to the decarburizing solution inlet of the lean liquid water cooler, the rich liquid inlet being connected to an outlet of the decarbonizing rich liquid with a lower temperature, the rich liquid outlet being connected to the rich liquid inlet of the regeneration tower. The lean-rich liquid heat exchanger being provided with a decarburizing solution channel and a rich liquid channel, the decarburizing solution channel being connected to the decarburizing solution inlet and the decarburizing solution outlet respectively and used for circulating the second stream of the decarburizing solution entering the lean-rich liquid heat exchanger, the rich liquid channel being connected to the rich liquid inlet and the rich liquid outlet respectively and used for circulating a rich liquid entering the lean-rich liquid heat exchanger.

According to the system of the present invention, the second decarburizing solution exchanges heat with a stream of a rich liquid having a lower temperature in the lean-rich liquid heat exchanger. The temperature of the rich liquid is increased by heat of the second stream of the decarburizing solution, and further steam needed for heating and desorption when the rich liquid is regenerated is reduced, which reduces energy consumption.

According to a preferred embodiment of the present invention, the second stream of the decarburizing solution and the rich liquid flow in countercurrent directions in the lean-rich liquid heat exchanger.

According to a preferred embodiment of the present invention, the lean liquid water cooler is provided therein with a decarburizing solution inlet, a decarburizing solution outlet, a washing water inlet, and a washing water outlet. The decarburizing solution inlet is connected to the decarburizing solution outlet of the lean-rich liquid heat exchanger, the decarburizing solution outlet being connected to a decarburizing solution inlet of a second absorption section, the washing water inlet being connected to a washing water outlet of a cooling section, the washing water outlet being connected to a washing water inlet of a water washing tower. The lean liquid water cooler is provided therein with a decarburizing solution channel and a washing water channel, the decarburizing solution channel being in communication with the decarburizing solution inlet and the decarburizing solution outlet respectively and used for circulating the second decarburizing solution entering the lean-rich liquid heat exchanger, the washing water channel being in communication with the washing water inlet and the washing water outlet respectively and used for circulating the washing water entering the lean liquid water cooler.

According to the system of the present invention, the second decarburizing solution exchanges heat with the washing water in the lean liquid water cooler. A temperature of the second decarburizing solution is decreased, so as to perform decarbonizing and cooling on the reaction gas. A temperature of the washing water is increased by the heat of the second decarburizing solution, and further the washing water enters the water washing tower to heat the reaction gas, so that heat is recycled.

According to a preferred embodiment of the present invention, the second decarburizing solution and the washing water flow in countercurrent directions in the lean liquid water cooler.

According to some embodiments of the present invention, the system further comprises a circulation bypass channel for directly mixing the reaction gas from which carbon dioxide is to be removed with a purified gas, and the circulation channel being provided with a first adjustment valve. An adjustment channel being connected in parallel to two ends of the first adjustment valve, and the adjustment channel being provided with a second adjustment valve.

According to a preferred embodiment of the present invention, the first adjustment valve allows passage of 100% of the reaction gas at maximum; and the second adjustment valve allows passage of 30% of the reaction gas at maximum.

According to another aspect of the present invention, use of the above system for removing carbon dioxide from a reaction gas is further provided.

According to some embodiments of the present invention, the use comprises the following steps:

step (1). performing a heating treatment on the reaction gas from which carbon dioxide is to be removed by heat exchanging the reaction gas with a washing water in a heating zone to obtain a gas stream iii;

step (2). performing a decarbonizing treatment on the gas stream iii obtained in step (1) and entering the decarbonizing zone by using a decarburizing solution to obtain a gas stream iv; and step (3). cooling the gas stream iv to obtain a $CO_2$-removed purified gas.

According to a preferred embodiment of the present invention, the step (1) comprises the following steps:

(1A). allowing a gas stream i, which is part of the reaction gas from which carbon dioxide is to be removed and enters the heating zone, to enter a gas heat exchanger, in which the gas stream i exchanges heat with a regeneration gas exiting from the top of a regeneration tower to obtain a gas stream ia;

(1B). allowing a gas stream ii, which is the other part of the reaction gas from which carbon dioxide is to be removed and enters the heating zone, to enter a water washing tower, in which the gas stream ii exchanges heat with the washing water to obtain a gas stream iia; and (1C). mixing the gas stream ia with the gas stream iia to obtain the gas stream iii which is delivered out of the heating zone.

According to a preferred embodiment of the present invention, a molar ratio of the gas stream i to the gas stream ii is (0-70):(100-30), preferably (30-70):(70-30), and more preferably (40-60):(60-40).

According to the use of the present invention, the gas stream i exchanges heat with the regeneration gas exiting from the top of the regeneration tower in the gas heat exchanger and absorbs heat in the regeneration gas, so that the temperature of the gas stream i is increased; and the gas stream ii exchanges heat with the washing water in the water washing tower and absorbs the heat in the washing water, so that the temperature of the gas stream ii is increased. On one hand, heat in the regeneration gas and in the washing water is used, so that the heat is recycled; and on the other hand, the temperature of the gas entering the absorption tower is increased. Further, a temperature of a rich liquid discharged from the absorption tower can be increased, and steam needed for heating and desorption when the rich liquid is regenerated is reduced, which saves energy and reduces energy consumption.

According to some embodiments of the present invention, in the step (2), the gas stream iii is allowed to enter the absorption tower to contact with the decarburizing solution counter-currently.

According to a preferred embodiment of the present invention, the step (2) comprises the following steps:

(2A). allowing the gas stream iii to enter a first absorption section of the absorption tower to countercurrent contact with a first stream of the decarburizing solution to obtain a gas stream iiia and a first stream of a rich liquid; and (2B). allowing the gas stream iiia to enter a second absorption section absorption tower to countercurrent contact with a second stream of the decarburizing solution to obtain the gas stream iv and a second stream of a rich liquid.

According to a preferred embodiment of the present invention, the washing water is desalted water. The washing water first passes through a cooling device to be cooled to a temperature below 40° C., then enters a cooling section of the absorption tower to exchange heat with the gas stream iv, then enters a lean liquid water cooler to exchange heat with the second stream of the decarburizing solution, and finally enters the washing tower to exchange heat with the gas stream ii. After that, the washing water returns to the cooling device again for cooling circulation.

According to the use of the present invention, the washing water first passes through the cooling device to be cooled to a temperature below 40° C. Then, the washing water enters the cooling section of the absorption tower to exchange heat with the gas stream iv and cool the gas stream iv, and the temperature of the washing water is increased. Then, the washing water enters the lean liquid water cooler to exchange heat with the second stream of the decarburizing solution and cool the second decarburizing solution, and the temperature of the washing water is further increased. Finally, the washing water enters the washing tower to exchange heat with the gas stream ii to transfer heat absorbed from the gas stream iv and the second stream of the decarburizing solution to the gas stream ii, so as to increase the temperature and humidity of the gas stream ii. After that, the washing water returns to the cooling device to continue the cooling circulation. In this process, the heat in the system is circulated and recycled by using the washing water as a medium, which reduces heat loss and saves energy.

With respect to the circumstance where the catalyst requires that a content of water in a circulation gas should be lower than 0.3% and chilled water must be provided to reduce a content of saturated water in the purified gas returning to a reactor, a chiller may be used to cool the washing water to a temperature below 33° C. for cooling a gas. In this way, the requirement of the catalyst can be met, and a great amount of steam needed by a lithium bromide chiller can also be saved without increasing energy consumption in decarbonizing.

According to a preferred embodiment of the present invention, the washing water from outside may be allowed to exchange heat with the gas stream ii, then passes through the cooling device to be cooled, then exchanges heat with the gas stream iv, and subsequently exchanges heat with the second stream of the decarburizing solution for circulation.

According to some embodiments of the present invention, the first stream of the decarburizing solution and the second stream of the decarburizing solution are a lean liquid from the bottom of the regeneration tower. The first stream of the decarburizing solution directly enters the first absorption section to countercurrent contact with the gas stream iii so as to obtain a first stream of a rich liquid. The second stream of the decarburizing solution first enters a lean-rich liquid heat exchanger to exchange heat with a stream of the rich liquid having a lower temperature, then enters the lean liquid water cooler to exchange heat with the washing water, and finally enters the second absorption section to countercurrent contact with the gas stream iiia so as to obtain a second stream of a rich liquid. The first stream of the rich liquid and the second stream of the rich liquid are mixed and returned to the regeneration tower for regeneration.

By heat exchanging the rich liquid having a lower temperature and the second stream of the decarburizing solution, on one hand, heat of the second stream of the decarburizing solution can be recycled and utilized, so that heat is recycled; and on the other hand, the temperature of the rich liquid is increased, so that steam needed for heating and desorption when the rich liquid is regenerated is reduced, which saves energy and reduces energy consumption.

According to some embodiments of the present invention, the use further comprises the following steps:

step (0). allowing a gas stream a', which is a part of the reaction gas, to be treated according to step (1) to step (3); and step (4). mixing the gas stream b', which is the other part of the reaction gas, to pass through a circulation channel so as to directly merge with a purified gas obtained according to step (1) to step (3), and recirculating back to the reactor.

According to a preferred embodiment of the present invention, the first adjustment valve and the second adjustment valve are controlled, so that a molar ratio of the gas stream a' to the gas stream b' is (70-100):(30-0), preferably (75-90):(25-10).

It is founded by the inventor during research that, by defining the ratio of the gas stream a' to the gas stream b' in the above range, a content of carbon dioxide in a gas circulating back to the reactor can be reduced significantly, or an amount of steam consumed when the rich liquid is regenerated is reduced.

It is found in research that, by using the technical solutions of the present invention, the amount of residual $CO_2$ in the purified gas can be greatly reduced, which meets the requirement of the new catalyst, and heat consumption in solution regeneration can also be reduced by more than 30%.

DETAILED DESCRIPTION OF THE EMBODIMENTS

The present invention is described in detail below in conjunction with the accompanying drawings and specific embodiments.

Figure 1:
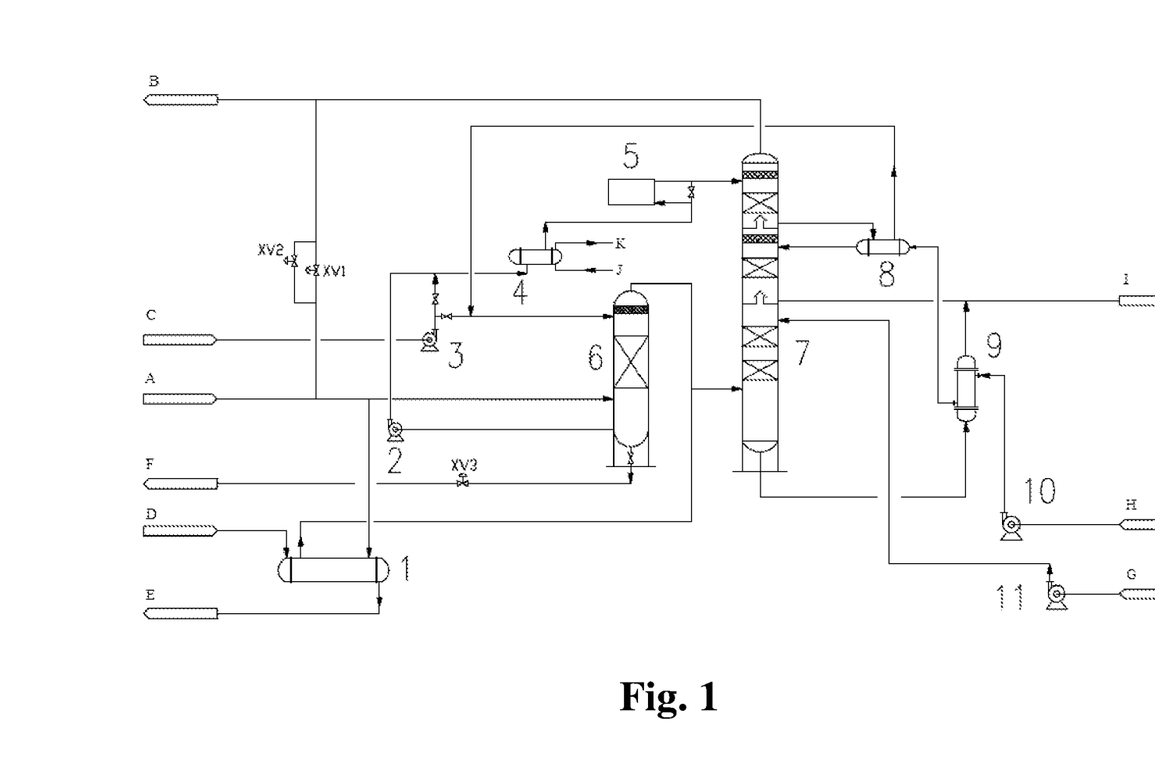
FIG. 1 shows a process flow diagram of a system according to an embodiment of the present invention.

As shown in FIG. 1, according to an embodiment of the present invention, a system for removing carbon dioxide in a reaction gas comprises a heating zone, a decarbonizing zone, a washing water cooling device, a decarburizing solution heat exchanging device, and a circulation gas bypass channel.

The heating zone comprises a gas heat exchanger 1 and a water washing tower 6.

The gas heat exchanger 1 is provided with a reaction gas inlet, a reaction gas outlet, a regeneration gas inlet, and a regeneration gas outlet. The reaction gas inlet is used for receiving the reaction gas from which carbon dioxide is to be removed, the reaction gas outlet being connected to a reaction gas inlet of an absorption tower in the decarbonizing zone, the regeneration gas inlet is connected to a gas outlet at a top of a regeneration tower, the regeneration gas outlet is connected to an inlet of a regeneration gas cooling device. The gas heat exchanger 1 is provided with a reaction gas channel and a regeneration gas channel. The reaction gas channel is connected to the reaction gas inlet and the reaction gas outlet respectively, and is used for circulating the reaction gas entering the gas heat exchanger. The regeneration gas channel is connected to the regeneration gas inlet and the regeneration gas outlet respectively, and is used for circulating the regeneration gas entering the gas heat exchanger.

The water washing tower 6 is provided with a reaction gas inlet, a reaction gas outlet, a washing water inlet, and a washing water outlet. The reaction gas inlet is used for receiving the reaction gas from which carbon dioxide is to be removed, the reaction gas outlet is connected to the reaction gas inlet of the absorption tower in the decarbonizing zone, the washing water inlet being connected to a washing water outlet of a lean liquid water cooler 8, the washing water outlet is connected to an inlet of a washing water cooling device. The reaction gas inlet of the water washing tower is provided at a lower portion of a sidewall thereof, the washing water outlet of the water washing tower being provided at a top thereof, the washing water inlet of the water washing tower being provided at an upper portion of the sidewall thereof, the washing water outlet of the water washing tower being provided at a lower portion of the sidewall thereof. The water washing tower is provided at the bottom thereof with a liquid waste outlet which is connected to a liquid waste discharge channel and is used for discharging liquid waste accumulated in the water washing tower. The liquid waste discharge channel is provided with a valve XV3. The washing water inlet of the water washing tower 6 is provided with a washing water supplement inlet connected thereto which is used for directly adding washing water into the water washing tower, and the washing water then enters a washing water cooler for circulation.

The decarbonizing zone comprises an absorption tower 7 which is used for performing decarbonizing and cooling treatment on the gas from the heating zone.

The absorption tower 7 is provided with a reaction gas inlet and a reaction gas outlet. The reaction gas inlet is connected to a gas outlet of a water washing tower in the decarbonizing zone and/or a gas outlet of a gas heat exchanger, and the reaction gas outlet is connected to a gas inlet of a reactor. The absorption tower 7 comprises a first absorption section, a second absorption section, and a cooling section disposed from the bottom to the top. The first absorption section, the second absorption section, and the cooling section are liquid-separated from one another by a liquid collection tray, and liquid is not allowed to pass through. The liquid collection tray is provided with a tray riser which allows the gas pass through. The first absorption section is provided with a reaction gas inlet, a reaction gas outlet, a decarburizing solution inlet, and a decarburizing solution outlet. The reaction gas inlet is connected to the reaction gas inlet of the absorption tower, the reaction gas outlet is connected to a reaction gas inlet of the second absorption section, preferably a tray riser of a liquid collection tray, the decarburizing solution inlet is connected to a liquid outlet at the bottom of the regeneration tower, the decarburizing solution outlet being connected to a rich liquid inlet of a lean-rich liquid heat exchanger 9. The reaction gas inlet of the first absorption section is provided at a lower portion of a sidewall thereof, the reaction gas outlet of the first absorption section being provided at the top thereof, preferably connected to a tray riser of a liquid collection tray, the decarburizing solution inlet of the first absorption section is provided at an upper portion of the sidewall thereof, the decarburizing solution outlet of the first absorption section is provided at the bottom thereof. The second absorption section is provided with a reaction gas inlet, a reaction gas outlet, a decarburizing solution inlet, and a decarburizing solution outlet. The reaction gas inlet is connected to the reaction gas outlet of the first absorption section, the reaction gas outlet is connected to a reaction gas inlet of the cooling section, preferably a tray riser of a liquid collection tray, the decarburizing solution inlet is connected to a decarburizing solution outlet of the lean liquid water cooler 8, the decarburizing solution outlet is connected to a rich liquid inlet of the regeneration tower. The reaction gas inlet of the second absorption section is provided at the bottom thereof, the reaction gas outlet of the second absorption section is provided at the top thereof, the decarburizing solution inlet of the second absorption section is provided at an upper portion of a sidewall thereof, the decarburizing solution outlet of the second absorption section being provided at a lower portion of the sidewall thereof. The cooling section is provided with a reaction gas inlet, a reaction gas outlet, a washing water inlet, and a washing water outlet. The reaction gas inlet is connected to the reaction gas outlet of the second absorption section, the reaction gas outlet being connected to the reaction gas outlet of the absorption tower, the washing water inlet is connected to a washing water outlet of a washing water cooling device, the washing water outlet is connected to a washing water inlet of the lean liquid water cooler. The reaction gas inlet of the cooling section is provided at the bottom thereof, the reaction gas outlet of the cooling section is provided at the top thereof, the washing water inlet of the cooling section is provided at an upper portion of a sidewall thereof, the washing water outlet of the cooling section is provided at a lower portion of the sidewall thereof.

The washing water cooling device is provided with a washing water inlet and a washing water outlet, and comprises a washing-water circulation-water cooler 4 and a washing-water chilled-water cooler 5 which are connected in series. The washing-water circulation-water cooler is provided with an inlet and an outlet, the inlet is connected to the washing water outlet of the water washing tower, the outlet is connected to an inlet of the washing-water chilled-water cooler. The washing-water chilled-water cooler is provided with an inlet and an outlet, the inlet is connected to the outlet of the washing-water circulation-water cooler, the outlet is connected to the washing water inlet of the cooling section of the absorption tower. According to a preferred embodiment of the present invention, the washing-water circulation-water cooler 4 is further provided with a washing water supplement inlet and a washing water discharge outlet, the washing water supplement inlet is used for supplementing desalted water to the system, the washing water discharge outlet is used for discharging washing water that is polluted in the system.

The decarburizing solution heat exchanging device comprises a lean-rich liquid heat exchanger 9 and a lean liquid water cooler 8. The lean-rich liquid heat exchanger 9 is used for heat exchanging the second stream of the decarburizing solution and the stream of a rich liquid having a lower temperature. The lean-rich liquid heat exchanger is provided with a decarburizing solution inlet, a decarburizing solution outlet, a rich liquid inlet, and a rich liquid outlet. The decarburizing solution inlet is connected to a liquid outlet at the bottom of the regeneration tower, the decarburizing solution outlet is connected to a decarburizing solution inlet of the lean liquid water cooler, the rich liquid inlet is connected to the decarburizing solution outlet of the first absorption section, the rich liquid outlet is connected to a rich liquid inlet of the regeneration tower. The lean-rich liquid heat exchanger is provided with a decarburizing solution channel and a rich liquid channel, the decarburizing solution channel is connected to the decarburizing solution inlet and the decarburizing solution outlet and used for circulating the second stream of the decarburizing solution entering the lean-rich liquid heat exchanger, the rich liquid channel is connected to the rich liquid inlet and the rich liquid outlet and used for circulating a rich liquid entering the lean-rich liquid heat exchanger. The lean liquid water cooler 8 is used for heat exchanging the second stream of the decarburizing solution with the washing water. The lean liquid water cooler is provided with a decarburizing solution inlet, a decarburizing solution outlet, a washing water inlet, and a washing water outlet. The decarburizing solution inlet is connected to the decarburizing solution outlet of the lean-rich liquid heat exchanger, the decarburizing solution outlet is connected to the decarburizing solution inlet of the second absorption section, the washing water inlet is connected to the washing water outlet of the cooling section, the washing water outlet is connected to the washing water outlet of the water washing tower. The lean liquid water cooler is provided with a decarburizing solution channel and a washing water channel, the decarburizing solution channel is connected to the decarburizing solution inlet and the decarburizing solution outlet respectively and used for circulating the second stream of the decarburizing solution entering the lean-rich liquid heat exchanger, the washing water channel is connected to the washing water inlet and the washing water outlet respectively and used for circulating the washing water entering the lean liquid water cooler.

The bypass channel is provided with a first adjustment valve XV1. An adjustment channel, which allows passage of 30% of an amount of the gas at maximum, is connected in parallel to two ends of the first adjustment valve, and is provided with a second adjustment valve XV2.

The system as shown in FIG. 1 works in the following process.

The reaction gas from an outlet of the reactor, after product separation, enters the system of the present invention. The gas stream i, a part of the reaction gas, enters the gas heat exchanger 1, and is heated by exchanging heat with the regeneration gas exiting from the top of the regeneration tower in the gas heat exchanger 1 to obtain the gas stream ia. The gas stream ii, the other part of the reaction gas, enters the water washing tower 6, and is heated and humidified by exchanging heat with the washing water to obtain the gas stream iia. The gas stream i and the gas stream ii are mixed to obtain the gas stream iii. The gas stream iii enters the first absorption section of the absorption tower 7, and countercurrent contacts with the first stream of the decarburizing solution to obtain the gas stream iiia and a first stream of a rich liquid. The gas stream iiia goes upward and enters the second absorption section of the absorption tower 7, and countercurrent contacts with the second stream of the decarburizing solution to obtain the gas stream iv and a second stream of a rich liquid. The gas stream iv goes upward further and enters the cooling section of the absorption tower 7, and is cooled by exchanging heat with the washing water to obtain a $CO_2$-removed purified gas. The purified gas circulates and returns to the reactor.

The lean liquid from the bottom of the regeneration tower is divided into two parts, i.e., the first stream of the decarburizing solution and the second stream of the decarburizing solution respectively. The first stream of the decarburizing solution directly enters the first absorption section, and countercurrent contacts with the gas stream iii to obtain a first stream of a rich liquid. The second stream of the decarburizing solution first enters the lean-rich liquid heat exchanger 9 and exchanges heat with the first stream of the rich liquid, then enters the lean liquid water cooler 8 and exchanges heat with the washing water, and finally enters the second absorption section and countercurrent contacts with the gas stream iiia to obtain a second stream of a rich liquid. Temperatures of the first stream of the rich liquid and the second stream of the rich liquid are increased, and the first stream of the rich liquid and the second stream of the rich liquid are mixed and, returned to the regeneration tower for regeneration.

The washing water is first cooled by the cooling device to a temperature below 40° C., then enters the cooling section of the absorption tower 7 and exchanges heat with the gas stream iv, subsequently enters the lean liquid water cooler 8 and exchanges heat with the second decarburizing solution, and finally enters the water washing tower 6 and exchanges heat with the gas stream ii. After that, the washing water is pressurized by a washing water circulation pump 2 and returns to the cooling device for cooling circulation. A content of impurities in the washing water is determined based on a result of real-time monitoring using a conductometer. If the content of impurities exceeds a set value, the valve XV3 is opened to discharge a part of liquid waste, and then new desalted water is supplemented through the washing water supplement inlet.

During normal operation, the valve XV1 is closed, and the valve XV2 is adjusted, so that 70%-100% of the total amount of the reaction gas enters the heating zone.

A system for removing carbon dioxide in a reaction gas shown in FIG. 2 and the system shown in FIG. 1 are substantively the same, and differ in the following aspects. The heating zone is composed of the washing tower 6 only. The washing-water chilled-water cooler 5 is replaced by a heat-pump lithium bromide chiller system 5', and a heat pump of the system 5' is in parallel connection with the gas heat exchanger. The regeneration gas from the regeneration tower enters the heat pump and supplies heat to the heat pump to generate steam; and the steam is supplied to the lithium bromide chiller for refrigeration, and the cold generated cools the washing water to a temperature below 33° C.

Figure 2:
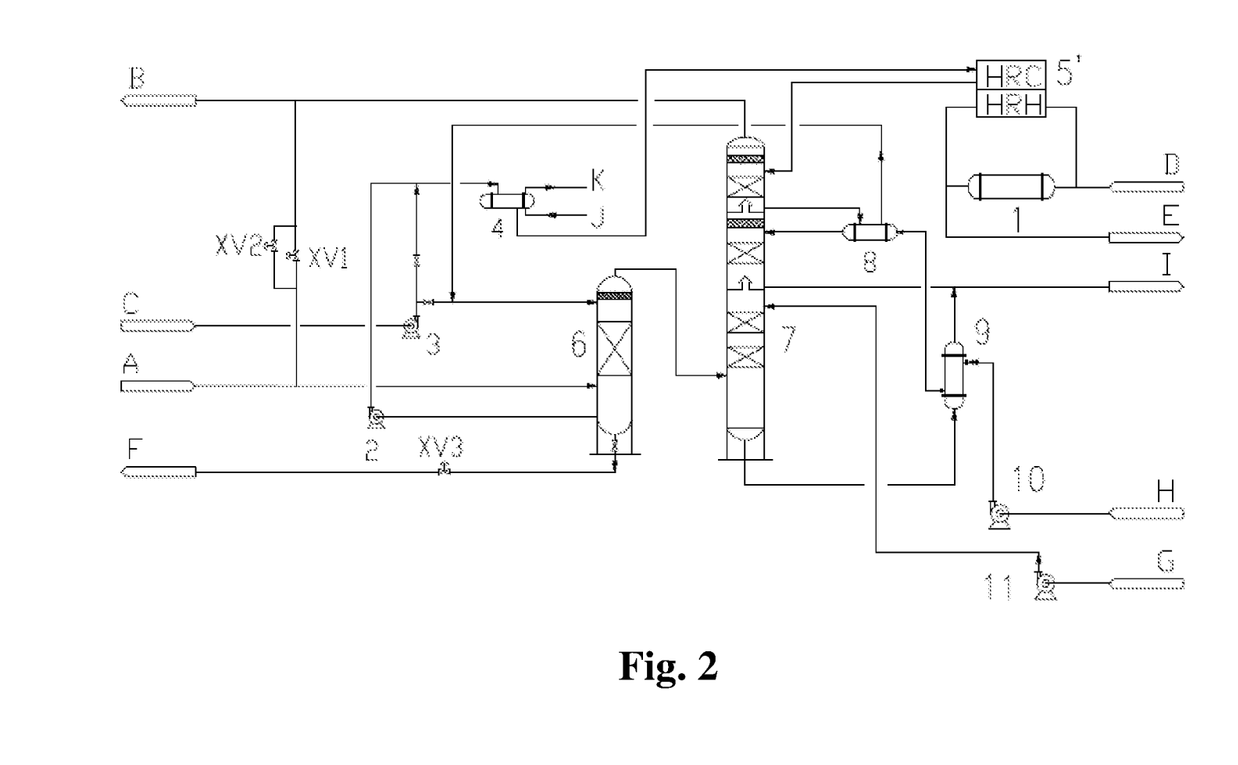
FIG. 2 shows a process flow diagram of a system according to another embodiment of the present invention.

The system as shown in FIG. 2 works in the following process.

The reaction gas from an outlet of the reactor, after product separation, enters the system of the present invention. The reaction gas enters the water washing tower 6, and is heated and humidified by exchanging heat with the washing water to obtain the gas stream iii. The gas stream iii enters the first absorption section of the absorption tower 7, and countercurrent contacts with the first stream of the decarburizing solution to obtain the gas stream iiia and a first stream of a rich liquid. The gas stream iiia goes upward and enters the second absorption section of the absorption tower 7, and countercurrent contacts with the second stream of the decarburizing solution to obtain the gas stream iv and a second stream of a rich liquid. The gas stream iv goes upward further and enters the cooling section of the absorption tower 7, and is cooled by exchanging heat with the washing water to obtain the $CO_2$-removed purified gas. The purified gas circulates and returns to the reactor.

The lean liquid from the bottom of the regeneration tower is divided into two parts, i.e., the first stream of the decarburizing solution and the second stream of the decarburizing solution respectively. The first stream of the decarburizing solution directly enters the first absorption section, and countercurrent contacts with the gas stream iii to obtain a first stream of a rich liquid. The second stream of the decarburizing solution first enters the lean-rich liquid heat exchanger 9 and exchanges heat with the first stream of the rich liquid, then enters the lean liquid water cooler 8 and exchanges heat with the washing water, and finally enters the second absorption section and countercurrent contacts with the gas stream iiia to obtain a second stream of a rich liquid. Temperatures of the first stream of the rich liquid and the second stream of the rich liquid are increased, and the first stream of the rich liquid and the second stream of the rich liquid, are mixed and returned to the regeneration tower for regeneration.

The washing water is first cooled by the washing-water circulation-water cooler 4 and the chiller 5' to a temperature below 33° C., then enters the cooling section of the absorption tower 7 and exchanges heat with the gas stream iv, subsequently enters the lean liquid water cooler 8 and exchanges heat with the second decarburizing solution, and finally enters the water washing tower 6 and exchanges heat with the gas stream ii. After that, the washing water is pressurized by the washing water circulation pump 2 and returns to the cooling device for cooling circulation. A content of impurities in the washing water is determined based on a result of real-time monitoring using the conductometer. If the content of impurities exceeds a set value, the valve XV3 is opened to discharge a part of liquid waste, and then new desalted water is supplemented through the washing water supplement inlet.

During normal operation, the valve XV1 is closed, and the valve XV2 is adjusted, so that 70%-100% of the total amount of the reaction gas enters the heating zone.

The regeneration gas from the regeneration tower enters the heat pump of the chiller 5' and supplies heat to the heat pump to generate steam, and the steam is supplied to the lithium bromide chiller for refrigeration.

Example 1

For an apparatus for synthesizing ethylene oxide from ethylene under the action of a silver catalyst with a scale of 70,000 ton/year, a decarbonizing unit for removing a by-product $CO_2$ produced in an oxidation synthesis reaction adopted a potassium carbonate decarbonizing process. In order to use a catalyst with high selectivity, it was required to reduce a concentration of $CO_2$ in a circulation gas at an inlet of the reactor from 2% to 1%. Accordingly, an amount of a reaction offgas entering a decarbonizing system was increased from 50% to 100%, i.e., from 83,654.2 kg/h to 164,284.7 kg/h.

The offgas was pressurized by a compressor, and a reaction gas with a pressure of 1.82 MPa (A) and a temperature of 56.5° C. entered the system of the present invention. A gas amount was 164,284.7 kg/h. In the reaction gas, a concentration of $CO_2$ was 1.59 mol %, a concentration of ethylene was 28.02 mol %, a concentration of $O_2$ was 5.86 mol %, and the remaining portion comprised $CH_4$, $C_2H_6$, $N_2$, Ar, and a small amount of steam and MEG. By using the process of the present invention, about 50% in molar fraction of the gas passed through a gas heat exchanger [1] and was heated to about 90° C. by recycling heat of a regeneration gas; the remaining gas entered a water washing tower [6] for heating and humidifying and was heated to about 85.5° C. by recycling heat of the washing water. The two portions of the gas were mixed to have a temperature of 87° C. and entered into an absorption tower [7]. The gas and a first stream of the decarburizing solution pumped by a carbonate pump [11] underwent countercurrent mass transfer absorption and heat exchange in filler of a first absorption section, and a first stream of a rich liquid exited from the absorption tower had a temperature of about 88.77° C. The first stream of the rich liquid passed through a lean-rich liquid heat exchanger [9] and exchanged heat with a second stream of the decarburizing solution having a temperature of 115° C., so that the first stream of the rich liquid was heated to about 103° C. The first stream of the rich liquid and a second stream of a rich liquid exited from a second absorption section were mixed and entered a flash tank at the top of a regeneration tower, and the mixed rich liquid had a temperature of 103.5° C., which was about 5° C. higher than a temperature before modification. In an ordinary hot potassium carbonate process, the reaction gas was allowed to enter the absorption tower [7], and the reaction gas and the first stream of the decarburizing solution pumped by the carbonate pump [11] underwent countercurrent mass transfer in filler of the first absorption section. The second stream of the decarburizing solution entered the second absorption section of the absorption tower and countercurrent contacted with the gas coming up from the first absorption section to remove $CO_2$. An absorbed rich liquid descended in the tower, and mixed with the first stream of the rich liquid, then returned to the regeneration tower for desorption and regeneration.

The second stream of the decarburizing solution pumped by the carbonate pump [10], was heat exchanged in the lean-rich liquid heat exchanger [9], entered a lean liquid water cooler [8] to exchange heat with circulation washing water, and was further cooled to about 80° C. after transferring heat to the washing water. The second stream of the decarburizing solution entered the second absorption section of the absorption tower and countercurrent contacted with the gas coming up from the first absorption section to remove $CO_2$, and a second stream of a rich liquid was obtained. The second stream of the rich liquid and the first stream of the rich liquid are mixed and returned to the regeneration tower for regeneration.

The circulation washing water from the washing tower [6] was pressurized by a washing water circulation pump [2]

and entered into a washing-water circulation-water cooler [4] for cooling, passed through a washing-water chilled-water cooler [5] to be cooled to below 35° C., entered a cooling section of the absorption tower to countercurrent contact with a purified gas exiting from the absorption tower so as to wash carbonate entrainment in the gas and transfer heat, reduced the temperature of the gas returning from the tower to the synthesis system below 37° C. The aim is to reduce a content of saturated steam (less than 0.3%) in the gas, so as to meet the requirement of the catalyst. The concentration of $CO_2$ in the gas at the inlet of the reactor was less than 1.0% (after the selectivity of the catalyst was improved, the concentration of $CO_2$ was less than 0.5%). In the ordinary hot potassium carbonate process, there was no water circulation system. The circulation gas directly entered the absorption tower, and the gas exited from the tower was cooled by a circulation water heat exchanger, all heat taken out by circulation water; and the decarburizing solution entering the absorption tower was also cooled by the circulation water, rather than by exchanging heat with the washing water, and no heat recycling was performed.

The washing water exited from the cooling section exchanged heat with the decarburizing solution in the lean liquid water cooler [8], and the washing water was heated to 88° C. and returned to the water washing tower [6] to countercurrent contact with the reaction gas entering the system for heat transfer and mass transfer in the filler. Trace organic substance in the circulation gas was washed, and the gas was heated and humidified. The gas was heated to about 85.5° C. and exited from the tower and mixed with another reaction gas and entered the absorption tower.

During normal operation, a valve XV1 was closed, and a valve XV2 was adjusted, so that about 86% of the total amount of the reaction gas to be treated entered the heating zone.

When 50% of the reaction offgas was decarbonized, steam needed for solution regeneration was about 15 t/h; and when 100% of the reaction offgas was decarbonized, by using the process of the present invention, increasing an amount of steam due to increase of a gas amount was not necessary, and about 10 t/h steam was saved in practice.

Comparative Example 1

For an apparatus for synthesizing ethylene oxide from ethylene under the action of a silver catalyst with a scale of 70,000 ton/year, a decarbonizing unit thereof for removing a by-product $CO_2$ produced in an oxidation synthesis reaction adopted a potassium carbonate decarbonizing process. An offgas was pressurized by a compressor, and a reaction gas with a pressure of 1.82 MPa (A) and a temperature of 56.5° C. entered a decarbonizing system. An amount of a circulation gas was 164,284.7 kg/h. In the offgas, a concentration of $CO_2$ was 1.59 mol %, a concentration of ethylene was 28.02 mol %, a concentration of $O_2$ was 5.86 mol %, and the remaining portion comprised $CH_4$, $C_2H_6$, $N_2$, Ar, and a small amount of steam and MEG. In order to reduce the concentration of $CO_2$ from current 2% to less than 1%, the reaction offgas entering the decarbonizing system is increased from 50% to 100%, i.e., the gas amount being increased from 83,654.2 kg/h to 164,284.7 kg/h.

By using the existing process, about 50% in molar fraction of the amount of the gas passed through an XV1 bypass and directly returned to a reactor (without entering the decarbonizing system), and the other about 50% of the amount of the gas passed through a gas heat exchanger [1] and was heated to about 90° C. by recycling heat of a regeneration gas, and then entered a carbon dioxide absorption tower. The tower comprised an upper portion and a lower portion which were connected to each other (without being liquid-separated). The gas and a decarburizing solution pumped by a carbonate pump underwent countercurrent mass transfer absorption and heat exchange in filler of the upper and lower portion. The decarburizing solution at an inlet of the upper section was cooled to 91° C. by external circulation cooling water (heat loss). The gas exiting from the absorption tower was cooled to 57.7° C. in a heat exchanger by external circulation cooling water (heat loss), and then was mixed with the reaction gas which did not enter the decarbonizing system but returned to a reaction system. A concentration of $CO_2$ in the gas was about 2.0%, which could not meet the requirement of the catalyst with high selectivity that the concentration of the $CO_2$ should be less than 1.0%. A decarbonizing rich liquid exiting from the absorption tower had a temperature of about 98.2° C. (heat was not recycled), and directly entered a flash tank at the top of a regeneration tower.

In order to meet the requirement of the catalyst that the concentration of the $CO_2$ in the gas at an inlet of the reactor should be less than 1.0%, 85%-100% of a circulation gas must be decarbonized. If the decarbonizing process was not modified according to Embodiment 1 and the original process was still used, steam consumption should be increased by about 10 tons (40%) based on current 15 ton/h.

Example 2

For a newly built apparatus for producing refined ethylene oxide from ethylene with a scale of 200,000 ton/year, an oxidation synthesis reaction was completed under the action of a silver catalyst, and a unit for removing a reaction by-product $CO_2$ adopted a hot potassium carbonate decarbonizing process.

A reaction circulation gas with a pressure of 2.38 MPa (A) and a temperature of 49.2° C. entered a decarbonizing system. An amount of a circulation gas was 668,822.04 kg/h. In the circulation gas, a concentration of $CO_2$ was 1.44 mol %, a concentration of ethylene was 28.61 mol %, a concentration of $O_2$ was 5.68 mol %, and the remaining portion comprised $CH_4$, $C_2H_6$, $N_2$, Ar, and a small amount of steam and MEG.

By using the process of the present invention, the gas entered a water washing tower [6] for heating and humidifying and was heated to about 69° C. by recycling heat in the washing water, and then entered an absorption tower [7]. No liquid separation plate was disposed between a second absorption section and a first absorption section of the absorption tower [7]. The gas and a decarburizing solution pumped by a carbonate pump [11] first underwent countercurrent mass transfer absorption and heat exchange in filler of the absorption tower at a lower portion of the absorption tower, and a rich liquid exited from the absorption tower had a temperature of about 72° C. The rich liquid passed through a lean-rich liquid heat exchanger [9] and exchanged heat with a decarburizing solution having a temperature of 105° C., so that the rich liquid was heated to about 95° C. and entered a flash tank at the top of a regeneration tower, thereby recycling heat that must be removed to decrease a temperature of a lean liquid.

After a decarburizing solution pumped by a carbonate pump [10] underwent heat exchange in the lean-rich liquid heat exchanger [9] so as to have a temperature of 75° C., the decarburizing solution entered a lean liquid water cooler [8] to exchange heat with circulation washing water. After heat was transferred to the washing water, the decarburizing solution was further cooled to 65° C., and the decarburizing solution entered the absorption tower and countercurrent contacted with the gas to remove $CO_2$ so as to meet a decarbonizing requirement.

The circulation washing water from the water washing tower [6] passed through a washing water circulation pump [2] to be pressurized, entered a washing-water circulation-water cooler [4] to be cooled, passed through a lithium bromide chiller to be cooled to a temperature below 33° C., entered a cooling section of the absorption tower to countercurrent contact with a purified gas exiting from the absorption tower for washing carbonate entrainment in the gas and heat transfer, thereby cooling the gas exited from the tower and returning to a synthesis system to a temperature below 37° C. The aim was to reduce a content of saturated steam in the gas (to be less than 0.3%), so as to meet the requirement of the catalyst. A concentration of $CO_2$ in the gas at an inlet of a reactor was less than 0.3%.

Washing water exiting from the cooling section exchanged heat with the decarburizing solution in a lean liquid water cooler [8], and the washing water heated to 70° C. returned to the water washing tower [6] to countercurrent contact with a reaction gas entering the system in the filler for heat transfer and mass transfer. Trace organic substance in the circulation gas was washed, and the gas was heated and humidified. The gas heated to about 69° C., exited from the tower and entered the absorption tower.

During normal operation, a valve XV1 was closed, and a valve XV2 was adjusted, so that about 85% of the total amount of the reaction gas to be treated entered the heating zone.

In the case that the same carbon dioxide removing effect was achieved, steam consumption was reduced from 40 ton/h in the ordinary hot potassium carbonate decarbonizing process (that is, decarbonizing treatment was performed on the reaction gas directly using a decarburizing solution without using a heat recycling measure) to below 20 ton/h, so that about 50% of steam was saved.

Example 3

For a newly built apparatus for producing ethylene oxide or glycol from ethylene with a scale of 800,000 ton/year, an oxidation synthesis reaction was completed under the action of a silver catalyst, and a unit for removing a reaction by-product $CO_2$ adopted a hot potassium carbonate decarbonizing process. A reaction gas with a pressure of 2.40 MPa (A) and a temperature of 56.6° C. entered a decarbonizing system. An amount of a circulation gas was 1,774,479.3 kg/h. In the reaction gas, a concentration of $CO_2$ was 1.71 mol %, a concentration of ethylene was 28.50 mol %, a concentration of $O_2$ was 5.97 mol %, and the remaining portion comprised $CH_4$, $C_2H_6$, $N_2$, Ar, and a small amount of steam and MEG. The process of the present invention was used, and procedures were substantively the same as those in Embodiment 2. Differences lie in the following aspects. The circulation washing water from the water washing tower [6] passed through a washing water circulation pump [2] to be pressurized, entered a washing-water circulation-water cooler [4] to be cooled, passed through a heat-pump lithium bromide chiller system 5' which used residual heat in a regeneration gas to cause a heat pump to generate steam which was provided to a lithium bromide chiller so as to cool the washing water to a temperature below 33° C., entered a cooling section of the absorption tower to countercurrent contact with a purified gas exited from the absorption tower so as to wash carbonate entrainment in the gas and transfer heat, thereby cooling the gas exited from the tower and returning to the synthesis system to below 37° C. The aim is to reduce a content of saturated steam (less than 0.3%) in the gas, so as to meet the requirement of the catalyst. The concentration of $CO_2$ in the gas at an inlet of the reactor was less than 1.0% (after the selectivity of the catalyst was improved, the concentration of $CO_2$ was less than 0.3%).

In the case that the same carbon dioxide removing effect was achieved, steam consumption was reduced from 76 ton/h in the ordinary hot potassium carbonate decarbonizing process to 46 ton/h, so that about 30 ton/h (about 40%) of steam was reduced.

Example 4

For an apparatus for producing ethylene oxide or glycol from ethylene with a scale of 50,000 ton/year, oxidation synthesis was completed under the action of a silver catalyst, and a unit for removing a reaction by-product $CO_2$ adopted a potassium carbonate decarbonizing process. A reaction gas with a pressure of 2.26 MPa (A) and a temperature of 48.4° C. entered a decarbonizing system. An amount of a circulation gas was 112,696.23 kg/h. In the reaction gas, a concentration of $CO_2$ was 2 mol %, a concentration of ethylene was 24.96 mol %, a concentration of $O_2$ was 5.99 mol %, and the remaining portion comprised $CH_4$, $C_2H_6$, $N_2$, Ar, and a small amount of EO and steam. The process of the present invention was used, and procedures were substantively the same as those in Embodiment 3. In the case that the same carbon dioxide removing effect was achieved, steam consumption was reduced by about 36% than that in the ordinary hot potassium carbonate decarbonizing process (that is, decarbonizing treatment was performed on the reaction gas directly using a decarburizing solution without using a heat recycling measure).

Example 5

For a newly built apparatus for producing vinyl acetate with a scale of 330,000 ton/year, ethylene, oxygen and acetic acid steam were subjected to a reaction under the action of a precious metal Pd—Au(Pt) catalyst and a potassium acetate cocatalyst and under conditions of 160-200° C. and 0.6-0.8 MPa, and a product was obtained after separation and rectification. A unit for removing a by-product $CO_2$ from this oxidation synthesis reaction adopted a potassium carbonate decarbonizing process. An offgas was pressurized by a compressor, and a circulation gas with a pressure of 1.2 MPa (A) and a temperature of 84° C. entered a decarbonizing system. A gas amount was 20,455.07 kg/h. In the circulation gas, a concentration of $CO_2$ was 14.94 mol %, a concentration of ethylene was 62.09 mol %, a concentration of $O_2$ was 3.24 mol %, and the remaining portion comprised $CH_4$, $C_2H_6$, $N_2$, Ar, and a small amount of steam. The process of the present invention was used, and procedures were substantively the same as those in Embodiment 3. In the case that the same carbon dioxide removing effect was achieved, steam consumption was reduced by about 35% than that in the ordinary hot potassium carbonate decarbonizing process (that is, decarbonizing treatment was performed on a reaction gas directly using a decarburizing solution without using a heat recycling measure).

Example 6

For a newly built apparatus for producing oil from coal with a scale of 1,000,000 ton/year, carbon monoxide and hydrogen were subjected to a reaction under the action of an iron catalyst and under conditions of 250-280° C. and 3.2-3.5 MPa in a slurry bed reactor, and a series of products comprised diesel oil were obtained after separation, hydrogenation, and rectification. A unit for removing a by-product $CO_2$ from this synthesis reaction adopted a potassium carbonate decarbonizing process. An offgas was pressurized by a compressor, and a circulation gas with a pressure of 3.5 MPa (A) and a temperature of 64° C. entered a decarbonizing system. A gas amount was 337,403.19 kg/h. In the circulation gas, a concentration of $CO_2$ was 12.93 mol %, a concentration of CO was 7.99 mol %, a concentration of $H_2$ was 58.72 mol %, and the remaining portion comprised $CH_4$, $C_2H_4$, $C_2H_6$, $N_2$, Ar, and a small amount of steam. The process of the present invention was used, and procedures were substantively the same as those in Embodiment 3. However, the washing-water circulation-water cooler and the washing-water chilled-water cooler in Embodiment 3 were replaced by an air cooling device. Referring to the composition of the decarburizing solution and regeneration procedures of the decarburizing solution in Chinese patent CN200610166303.6, in the case that the same carbon dioxide removing effect was achieved, steam consumption was reduced by about 37% than that in the ordinary hot potassium carbonate decarbonizing process (that is, decarbonizing treatment was performed on a reaction gas directly using a decarburizing solution without using a heat recycling measure).

Example 7

For an apparatus for producing oil from coal with a scale of 2,000,000 ton/year, carbon monoxide and hydrogen were subjected to a reaction under the action of an iron catalyst and under conditions of 260-280° C. and 2.8-3.0 MPa in a slurry bed reactor, and a series of products comprised diesel oil were obtained after separation, hydrogenation, and rectification. A unit for removing a by-product $CO_2$ from this synthesis reaction adopted a potassium carbonate decarbonizing process. A circulation gas with a pressure of 2.72 MPa (A) and a temperature of 40° C. entered a decarbonizing system. A gas amount was 430,402.82 kg/h. In the circulation gas, a concentration of $CO_2$ was 14.71 mol %, a concentration of CO was 7.11 mol %, a concentration of $H_2$ was 60.55 mol %, and the remaining portion comprised $CH_4$, $C_2H_4$, $C_2H_6$, $N_2$, Ar, and a small amount of steam. The process of the present invention was used, and procedures were substantively the same as those in Embodiment 6. Referring to the composition of the decarburizing solution and regeneration procedures of the decarburizing solution in Chinese patent CN200610166303.6, in the case that the same carbon dioxide removing effect was achieved, steam consumption was reduced by about 36% than that in the ordinary hot potassium carbonate decarbonizing process (that is, decarbonizing treatment was performed on a reaction gas directly using a decarburizing solution without using a heat recycling measure).

Example 8

For an apparatus for producing oil from coal with a scale of 1,000,000 ton/year, carbon monoxide and hydrogen were subjected to a reaction under the action of an iron catalyst and under conditions of 240-280° C. and 2.6-2.8 MPa in a slurry bed reactor, and a series of products comprised diesel oil were obtained after separation, hydrogenation, and rectification. A unit for removing a by-product $CO_2$ from this synthesis reaction adopted a potassium carbonate decarbonizing process. A circulation gas with a pressure of 1.8 MPa (A) and a temperature of 40° C. entered a decarbonizing system. A gas amount was 376,081.41 kg/h. In the circulation gas, a concentration of $CO_2$ was 15.8 mol %, a concentration of CO was 19.18 mol %, a concentration of $H_2$ was 34.86 mol %, and the remaining portion comprised $CH_4$, $C_2H_4$, $C_2H_6$, $N_2$, Ar, and a small amount of steam. The process of the present invention was used, and procedures were substantively the same as those in Embodiment 6. Referring to the composition of the decarburizing solution and regeneration procedures of the decarburizing solution in Chinese patent CN200610166303.6, in the case that the same carbon dioxide removing effect was achieved, steam consumption was reduced by about 30% than that in the ordinary hot potassium carbonate decarbonizing process (that is, decarbonizing treatment was performed on a reaction gas directly using a decarburizing solution without using a heat recycling measure).

Example 9

For an apparatus for producing oil from coal with a scale of 1,000,000 ton/year, carbon monoxide and hydrogen were subjected to a reaction under the action of an iron catalyst and under conditions of 250-280° C. and 3.2-3.5 MPa in a slurry bed reactor, and a series of products comprised diesel oil were obtained after separation, hydrogenation, and rectification. A unit for removing a by-product $CO_2$ from this synthesis reaction adopted a potassium carbonate decarbonizing process. An offgas was pressurized by a compressor, and a circulation gas with a pressure of 3.45 MPa (A) and a temperature of 77.2° C. entered a decarbonizing system. A gas amount was 208,014.11 kg/h. In the circulation gas, a concentration of $CO_2$ was 14.31 mol %, a concentration of CO was 7.07 mol %, a concentration of $H_2$ was 58.86 mol %, and the remaining portion comprised $CH_4$, $C_2H_4$, $C_2H_6$, $N_2$, Ar, and a small amount of steam.

The process of the present invention was used, and procedures were substantively the same as those in Embodiment 6. Referring to the composition of the decarburizing solution and regeneration procedures of the decarburizing solution in Chinese patent CN200610166303.6, in the case that the same carbon dioxide removing effect was achieved, steam consumption was reduced by about 33% than that in the ordinary hot potassium carbonate decarbonizing process (that is, decarbonizing treatment was performed on a reaction gas directly using a decarburizing solution without using a heat recycling measure).

Example 10

For an apparatus for producing oil from coal with a scale of 1,000,000 ton/year, carbon monoxide and hydrogen were subjected to a reaction under the action of an iron catalyst and under conditions of 260-280° C. and 2.70-2.80 MPa in a slurry bed reactor, and a series of products comprised diesel oil were obtained after separation, hydrogenation, and rectification. A unit for removing a by-product $CO_2$ from this synthesis reaction adopted a potassium carbonate decarbonizing process. A circulation gas with a pressure of 2.72 MPa (A) and a temperature of 42° C. entered a decarbonizing system. A gas amount was 220,411.71 kg/h. In the circulation gas, a concentration of $CO_2$ was 11.86 mol %, a concentration of CO was 8.09 mol %, a concentration of $H_2$ was 66.98 mol %, and the remaining portion comprised $CH_4$, $C_2H_4$, $C_2H_6$, $N_2$, Ar, and a small amount of steam. The process of the present invention was used, and procedures were substantively the same as those in Embodiment 6. Referring to the composition of the decarburizing solution and regeneration procedures of the decarburizing solution in Chinese patent CN200610166303.6, in the case that the same carbon dioxide removing effect was achieved, steam consumption was reduced by about 35% than that in the ordinary hot potassium carbonate decarbonizing process (that is, decarbonizing treatment was performed on a reaction gas directly using a decarburizing solution without using a heat recycling measure).

Example 11

For an apparatus for producing oil from coal with a scale of 1,000,000 ton/year, carbon monoxide and hydrogen were subjected to a reaction under the action of an iron catalyst and under conditions of 260-280° C. and 2.8-3.0 MPa in a slurry bed reactor, and a series of products comprised diesel oil were obtained after separation, hydrogenation, and rectification. A unit for removing a by-product $CO_2$ from this synthesis reaction adopted a potassium carbonate decarbonizing process. A circulation gas with a pressure of 2.72 MPa (A) and a temperature of 42.6° C. entered a decarbonizing system. A gas amount was 204644.42 kg/h. In the circulation gas, a concentration of $CO_2$ was 14.16 mol %, a concentration of CO was 7.05 mol %, a concentration of $H_2$ was 64.46 mol %, and the remaining portion comprised $CH_4$, $C_2H_4$, $C_2H_6$, $N_2$, Ar, and a small amount of steam. The process of the present invention was used, and procedures were substantively the same as those in Embodiment 6. Referring to the composition of the decarburizing solution and regeneration procedures of the decarburizing solution in Chinese patent CN200610166303.6, in the case that the same carbon dioxide removing effect was achieved, steam consumption was reduced by about 36% than that in the ordinary hot potassium carbonate decarbonizing process (that is, decarbonizing treatment was performed on a reaction gas directly using a decarburizing solution without using a heat recycling measure).

Example 12

For an apparatus for producing oil from coal with a scale of 2,000,000 ton/year, carbon monoxide and hydrogen were subjected to a reaction under the action of an iron catalyst and under conditions of 250-280° C. and 3.2-3.5 MPa in a slurry bed reactor, and a series of products comprised diesel oil were obtained after separation, hydrogenation, and rectification. A unit for removing a by-product $CO_2$ from this synthesis reaction adopted a potassium carbonate decarbonizing process. An offgas was pressurized by a compressor, and a circulation gas with a pressure of 3.53 MPa (A) and a temperature of 85.6° C. entered a decarbonizing system. A gas amount was 379,240.51 kg/h. In the circulation gas, a concentration of $CO_2$ was 13.99 mol %, a concentration of CO was 7.75 mol %, a concentration of $H_2$ was 61.15 mol %, and the remaining portion comprised $CH_4$, $C_2H_4$, $C_2H_6$, $N_2$, Ar, and a small amount of steam.

The process of the present invention was used, and procedures were substantively the same as those in Embodiment 6. Referring to the composition of the decarburizing solution and regeneration procedures of the decarburizing solution in Chinese patent CN200610166303.6, in the case that the same carbon dioxide removing effect was achieved, steam consumption was reduced by about 32% than that in the ordinary hot potassium carbonate decarbonizing process (that is, decarbonizing treatment was performed on a reaction gas directly using a decarburizing solution without using a heat recycling measure).

Example 13

For an apparatus for producing oil from coal with a scale of 600,000 ton/year, carbon monoxide and hydrogen were subjected to a reaction under the action of an iron catalyst and under conditions of 260-280° C. and 2.8-3.0 MPa in a slurry bed reactor, and a series of products comprised diesel oil were obtained after separation, hydrogenation, and rectification. A unit for removing a by-product $CO_2$ from this synthesis reaction adopted a potassium carbonate decarbonizing process. A circulation gas with a pressure of 2.63 MPa (A) and a temperature of 41.8° C. entered a decarbonizing system. A gas amount was 145,378.06 kg/h. In the circulation gas, a concentration of $CO_2$ was 12.85 mol %, a concentration of CO was 9.04 mol %, a concentration of $H_2$ was 61.49 mol %, and the remaining portion comprised $CH_4$, $C_2H_4$, $C_2H_6$, $N_2$, Ar, and a small amount of steam. The process of the present invention was used, and procedures were substantively the same as those in Embodiment 6. Referring to the composition of the decarburizing solution and regeneration procedures of the decarburizing solution in Chinese patent CN200610166303.6, in the case that the same carbon dioxide removing effect was achieved, steam consumption was reduced by about 38% than that in the ordinary hot potassium carbonate decarbonizing process (that is, decarbonizing treatment was performed on a reaction gas directly using a decarburizing solution without using a heat recycling measure).

For any numerical values mentioned in the present invention, if there are only two units between a minimum value and a maximum value, then all values increased by one unit per time between the minimum value and the maximum value are included. For example, if it is claimed that an amount of a component or a value of a process variable such as temperature, pressure, and time is 50-90, it means, in the present description, that values such as 51-89, 52-88, . . . 69-71, and 70-71 are listed specifically. For non-integral values, 0.1, 0.01, 0.001, or 0.0001 may be properly considered as a unit. These are only some specifically stated examples. In the present application, in a similar way, all possible combinations of listed values between the minimum value and the maximum value are considered as having been disclosed.

It should be noted that, the above described embodiments are only for explaining the present invention, and do not constitute any limitation to the present invention. The present invention is described in conjunction with exemplary embodiments, but it should be appreciated that words used herein are descriptive and explanatory, rather than restrictive. Modification can be made to the present invention within the scope of the present invention according to stipulations, and amendment can be made to the present invention without departing from the scope and spirit of the present invention. Although the description of the present invention relates to specific methods, materials and embodiments, it does not mean that the present invention is limited to specific embodiments disclosed herein. On the contrary, the present invention can expand to all other methods and applications having the same functions.

LIST OF REFERENCE NUMBERS

1 . . . gas heat exchanger
2 . . . washing water circulation pump

3 . . . desalted water booster pump
4 . . . washing-water circulation-water cooler
5 . . . washing-water chilled-water cooler
5' . . . heat-pump lithium bromide chiller system
6 . . . water washing tower
7 . . . absorption tower
8 . . . lean liquid water cooler
9 . . . lean-rich liquid heat exchanger
10 . . . decarburizing solution pump-2
11 . . . decarburizing solution pump-1
A . . . reaction gas for removing carbon dioxide
B . . . purified gas
C . . . desalted water
D . . . regeneration gas from the top of a regeneration tower
E . . . regeneration gas returning to a regeneration gas cooler
F . . . liquid waste to be treated
G . . . lean liquid from the bottom of a regeneration tower
F . . . lean liquid from the bottom of a regeneration tower
I . . . rich liquid going to a regeneration tower
J . . . circulation washing water feeding
K . . . circulation washing water discharging

The invention claimed is:

1. A method for removing carbon dioxide from a reaction gas, comprising:
S1. performing a heating treatment on a reaction gas from which carbon dioxide is to be removed by heat exchanging the reaction gas with a washing water and a regeneration gas; and the step S1 comprises the following steps:
1A. dividing the reaction gas from which carbon dioxide is to be removed into a gas stream I and a gas stream II;
1B. heating the gas stream I by heat exchanging with a regeneration gas exiting from a top of a regeneration tower to obtain a gas stream Ia;
1C. heating the gas stream II by heat exchanging with the washing water to obtain a gas stream IIa; and
1D. mixing the gas stream Ia with the gas stream IIa to obtain the gas stream III;
S2. performing a decarbonizing treatment on the gas stream III obtained in step S1 by using a decarburizing solution to obtain a gas stream IV; and
S3. cooling the gas stream IV to obtain a $CO_2$-removed purified gas,
wherein the washing water is first cooled by a cooling device, then exchanges heat with the gas stream IV, subsequently exchanges heat with the decarburizing solution, finally exchanges heat with the reaction gas from which carbon dioxide is to be removed, and after that returns to the cooling device for cooling circulation.

2. The method according to claim 1, wherein a molar ratio of the gas stream I to the gas stream II is (0-70):(100-30).

3. The method according to claim 1, wherein the decarburizing solution is a lean liquid from a bottom of a regeneration tower; and the step S2 comprises the following steps:
2A. allowing the gas stream III to countercurrent contact with a first stream of the decarburizing solution to obtain a gas stream IIIa and a first stream of a rich liquid; and
2B. allowing the gas stream IIIa to countercurrent contact with a second stream of the decarburizing solution to obtain the gas stream IV and a second stream of a rich liquid.

4. The method according to claim 3, wherein the first stream of the decarburizing solution and the second stream of the decarburizing solution are the lean liquid from the bottom of the regeneration tower; the first stream of the decarburizing solution directly countercurrent contacts with the gas stream III to obtain the first stream of the rich liquid; the second stream of the decarburizing solution first exchanges heat with a stream of the rich liquid having a lower temperature, then exchanges heat with a circulation washing water, and finally countercurrent contacts with the gas stream IIIa to obtain the second stream of the rich liquid; and the first stream of the rich liquid and the second stream of the rich liquid return to the regeneration tower for regeneration.

5. The method according to claim 1, wherein the method further comprises:
by using heat contained in a regeneration gas exiting from the top of a regeneration tower, providing heat to a lithium bromide chiller of a cooling device to generate chilled-water, decreasing the temperature of the washing water by the chilled-water, and then cooling the gas stream IV.

6. The method according to claim 1, wherein the method further comprises the following steps:
S0. dividing the reaction gas from a compressor into a gas stream A' and a gas stream B', the gas stream A' being treated according to the steps S1 to S3; and
S4. mixing the gas stream B' with the $CO_2$-removed purified gas obtained according to the steps S1 to S3 and recirculating back to the reactor.

7. The method according to claim 6, wherein a molar ratio of the gas stream A' to the gas stream B' is (70-100):(30-0).

8. The method according to claim 2, wherein the molar ratio of the gas stream I to the gas stream II is (30-70):(70-30).

9. The method according to claim 2, wherein the molar ratio of the gas stream I to the gas stream II is (40-60):(60-40).

10. The method according to claim 3, wherein the decarburizing solution is a carbonate solution.

11. The method according to claim 7, wherein the molar ratio of the gas stream A' to the gas stream B' is (75-90):(25-10).

* * * * *